US011246806B1

(12) United States Patent
Kearns et al.

(10) Patent No.: US 11,246,806 B1
(45) Date of Patent: Feb. 15, 2022

(54) SYSTEM AND MEDICATION BOX FOR IMPROVING MEDICATION ADHERENCE

(71) Applicants: William Diehl Kearns, Tampa, FL (US); Kimberly Ann Crosland, Lithia, FL (US); Jeffrey D. Craighead, Groveland, FL (US); James Leonard Fozard, Palm Harbor, FL (US)

(72) Inventors: William Diehl Kearns, Tampa, FL (US); Kimberly Ann Crosland, Lithia, FL (US); Jeffrey D. Craighead, Groveland, FL (US); James Leonard Fozard, Palm Harbor, FL (US)

(73) Assignees: THE UNITED STATES GOVERNMENT AS REPRESENTED BY THE DEPARTMENT OF VETERANS AFFAIRS, Washington, DC (US); UNIVERSITY OF SOUTH FLORIDA, Tampa, FL (US)

( * ) Notice: Subject to any disclaimer, the term of this patent is extended or adjusted under 35 U.S.C. 154(b) by 439 days.

(21) Appl. No.: 15/802,635

(22) Filed: Nov. 3, 2017

Related U.S. Application Data

(60) Provisional application No. 62/417,043, filed on Nov. 3, 2016.

(51) Int. Cl.
*A61J 7/04* (2006.01)
*G06K 19/06* (2006.01)
(Continued)

(52) U.S. Cl.
CPC ........... *A61J 7/0481* (2013.01); *A61J 7/0092* (2013.01); *G06K 19/06028* (2013.01);
(Continued)

(58) Field of Classification Search
CPC .... A61J 7/0481; A61J 7/0092; A61J 2200/30; A61J 7/0445; A61J 7/0076; A61J 7/0069;
(Continued)

(56) References Cited

U.S. PATENT DOCUMENTS 6,169,707 B1 * 1/2001 Newland ............... A61J 7/0481
221/2
9,427,377 B1 * 8/2016 Miceli ....................... A61J 7/04
(Continued)

OTHER PUBLICATIONS

Chan M, et al., Adverse drug events as a cause of hospital admission in the elderly. Internal Medicine Journal. 2001;31(4):199-205.
(Continued)

*Primary Examiner* — J. Gregory Pickett
*Assistant Examiner* — Jenine Pagan
(74) *Attorney, Agent, or Firm* — Meunier Carlin & Curfman LLC

(57) ABSTRACT

A medication adherence system and corresponding medication box for improving medication adherence. The system includes the medication box, which is transparent and has a machine-readable marker, such as a QR code, on or beneath the floor thereof. The marker is capable of being scanned and read through the transparent bottoms of individual chambers. Data embedded in the marker includes, but is not limited to, the user's medication plan, the date and time when the medication is to be ingested, and instructions for recording the date and time when the marker is scanned and read. The underlying software program/application processes this information and provides an indication as to the user's compliance with the medication plan.

10 Claims, 6 Drawing Sheets

(51) Int. Cl.
*A61J 7/00* (2006.01)
*G16H 20/13* (2018.01)
*G16H 70/40* (2018.01)

(52) U.S. Cl.
CPC .......... *A61J 7/0069* (2013.01); *A61J 7/0076* (2013.01); *A61J 7/0418* (2015.05); *A61J 7/0445* (2015.05); *A61J 2200/30* (2013.01); *G16H 20/13* (2018.01); *G16H 70/40* (2018.01)

(58) Field of Classification Search
CPC .. A61J 7/0418; G06F 19/326; G06F 19/3462; G06K 19/06028; G16H 70/40; G16H 20/13
USPC ............................. 206/528, 534, 534.1, 538
See application file for complete search history.

(56) References Cited

U.S. PATENT DOCUMENTS

| | | | |
|---|---|---|---|
| 9,934,366 B1* | 4/2018 | Zanuzoski | G16H 20/13 |
| 2007/0023316 A1* | 2/2007 | Coe | A61J 1/03 |
| | | | 206/534 |
| 2009/0206100 A1* | 8/2009 | Mazur | A61J 7/0069 |
| | | | 221/1 |
| 2012/0305584 A1* | 12/2012 | Carson | A61J 1/035 |
| | | | 221/1 |
| 2014/0042052 A1* | 2/2014 | Tsai | A61J 1/03 |
| | | | 206/534 |
| 2014/0214438 A1* | 7/2014 | Ahmadi | A61J 1/035 |
| | | | 705/2 |
| 2014/0251861 A1* | 9/2014 | Priebe | A61J 1/03 |
| | | | 206/534 |
| 2014/0346068 A1* | 11/2014 | Omura | A61B 50/00 |
| | | | 206/363 |
| 2016/0000657 A1* | 1/2016 | Dickie | A61J 7/0084 |
| | | | 206/534 |
| 2016/0074284 A1* | 3/2016 | Despa | A61J 7/0409 |
| | | | 340/573.1 |
| 2016/0143807 A1* | 5/2016 | Ika | A61J 1/03 |
| | | | 206/216 |
| 2016/0324725 A1* | 11/2016 | Horn | A61J 7/04 |
| 2017/0087059 A1 | 3/2017 | Rodriguez et al. | |

OTHER PUBLICATIONS

Parameswaran Nair N, et al., Hospitalization in older patients due to adverse drug reactions—the need for a prediction tool. Clinical Interventions in Aging. 2016;11:497-505.

Dapcich-Miura E, et al. Contingency management of adherence to a complex medical regimen in an elderly heart patient. Behavior Therapy. 1979;10(2):193-201.

* cited by examiner

PAPER WITH QR CODES

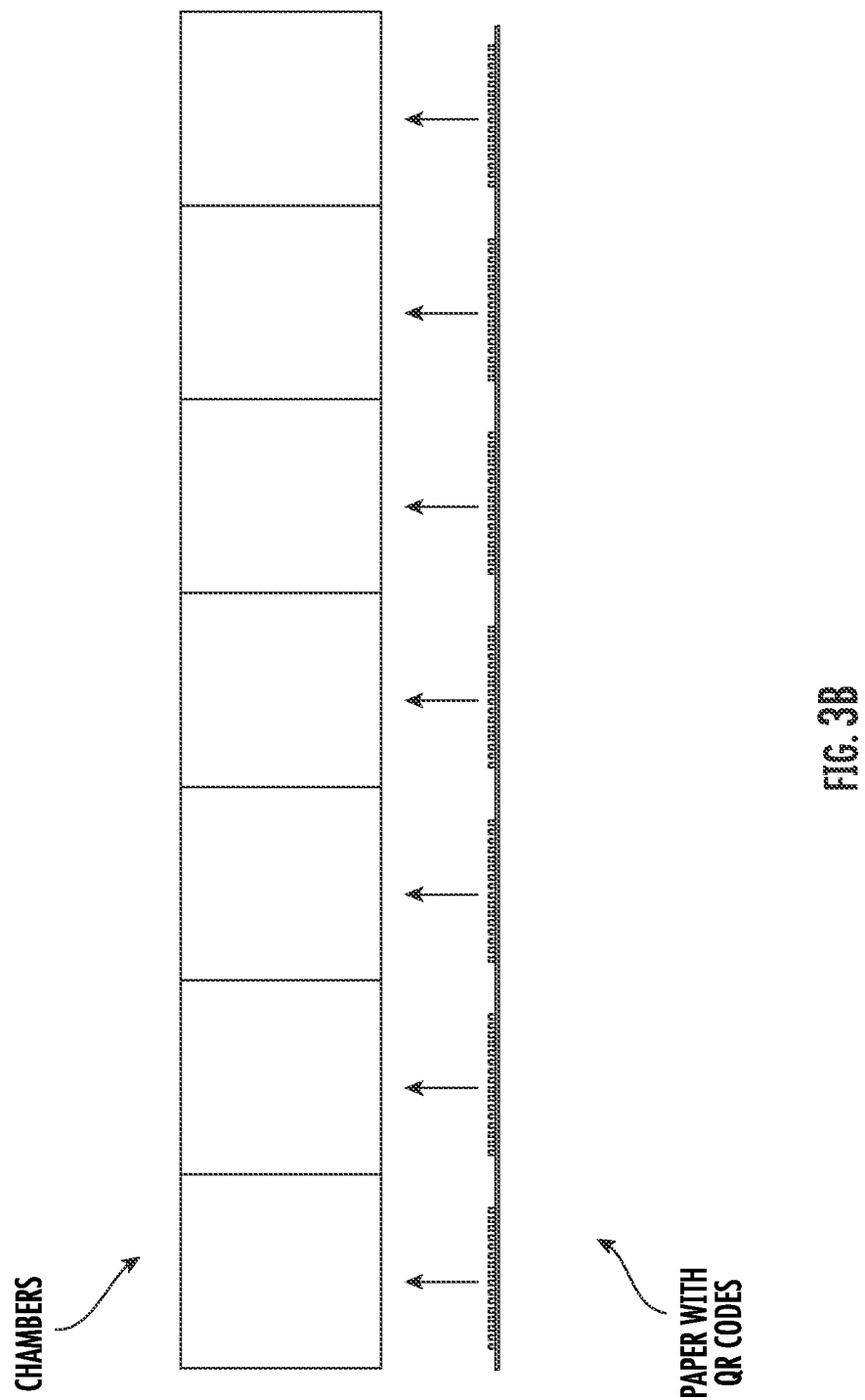

SYSTEM AND MEDICATION BOX FOR IMPROVING MEDICATION ADHERENCE

CROSS-REFERENCE TO RELATED APPLICATIONS

This nonprovisional application claims priority to U.S. Provisional Patent Application No. 62/417,043, entitled "Machine Readable Marker Based Medication Adherence App", filed Nov. 3, 2016 by the same inventors, the entirety of which is incorporated herein by reference.

BACKGROUND OF INVENTION

1. Field of the Invention

This invention relates to medication adherence. Specifically, the invention describes a machine-readable marker medication adherence app.

2. Brief Description of the Prior Art

As many as 26% of hospital admissions have been revealed to be due to medication noncompliance and omission of medication or cessation of indicated treatment, and 53.4% of these instances were found to be preventable [Chan M, et al., Adverse drug events as a cause of hospital admission in the elderly. Internal Medicine Journal. 2001; 31(4):199-205]. A more recent comprehensive review [Parameswaran Nair N, et al., Hospitalization in older patients due to adverse drug reactions—the need for a prediction tool. Clinical Interventions in Aging. 2016; 11:497-505] found that adverse drug reactions in elderly persons may be responsible for as many as 12% of all hospital admissions. Preventable adverse drug events increase the costs of medical care by increasing length of stay, necessitating subsequent rehabilitation, and adding stress, pain, and suffering for caregivers. In 12% of these cases, the unnecessary admissions can be traced to a failure to comply with physician prescribed medication regimens.

Advances in automation have led to smart medication boxes to prompt and record medication compliance in the home. However, these devices are typically very expensive, have complex interfaces challenging even normal elders and vex those with diminished cognitive capacity due to their medical conditions. Furthermore, these devices only signal medications should be taken, but deliver no consequences to sustain motivation. This design oversight generates compliance rates hovering at 60 to 70% even with automated prompting—rates that should be much higher based upon behavioral research on medication compliance that has shown that repeatedly delivering positive reinforcers contingent on medication-taking behaviors increases compliance by over 20% in normal adults/elderly [Dapcich-Miura E, et al. Contingency management of adherence to a complex medical regimen in an elderly heart patient. Behavior Therapy. 1979; 10(2):193-201]. However, conventional technologies that are prompting-only compliance-enhancing technologies have largely ignored these findings or otherwise have not maximized the benefits or effectiveness thereof.

A fusion of behavioral technology with automation is required to achieve the promise of these medication devices; hardware development alone is not the answer, but the procedural technology that is employed is of overarching importance. Accordingly, what is needed is an improved pill/tablet box that facilitates medication compliance. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved mechanism of enhancing medication compliance is now met by a new, useful, and nonobvious invention.

In an embodiment, the current invention is a system for medication compliance, comprising a medication box and an array of machine-readable markers (e.g., QR codes). The medication box includes an array of sequentially-ordered chambers and lid(s) for covering the top sides of the chambers. In certain embodiments, each chamber's bottom can be transparent. The markers are disposed on the bottom sides of or underneath all the chambers; there is one marker per chamber. Each marker is embedded with data pertaining to a medication plan of a user of the medication box, wherein the medication plan includes identification of medication to be contained within a corresponding chamber, a date and time that the medication is scheduled to be ingested by the user, and instructions to record a date and time at which the machine-readable marker is scanned and read. The marker is read on the bottom of the chamber or through a transparent chamber. In one embodiment, the marker can be laser engraved or laser etched onto the bottom sides of each chamber. In another embodiment, the marker can be placed within the chamber with a cover disposed in overlying relation thereto. These marker covers should be transparent to permit access to the underlying markers. Finally, the marker may be placed on the bottom side of a transparent medication box.

The system further includes a non-transitory computer readable storage media having computer-executable instructions, when executed by a processor, performing a method for processing the data embedded on each machine-readable marker. The instructions include receiving an image of the marker as a result of a chamber being emptied of the medication by the user and the user capturing an image of the marker, which prior to medication ingestion was obscured beneath the medication and therefore unreadable. The marker is decoded, and data embedded thereon is extracted. The date and time that the medication is scheduled to be ingested by the user is compared with the date and time at which the machine-readable marker was scanned and read. Using this comparison, it is determined whether the user consumed the medication according to the medication plan that was preset for him/her. Optionally, the media may further include a reinforcement system, such as a token economy module and/or monetary reinforcement protocols, operating via applied behavior analysis technology. In other embodiments, the instructions may further include storing comparisons of times and determinations of medication compliance, generating a historical log of long-term medication compliance by the user, and outputting the historical log onto a platform. This historical log/platform may be accessed by the user or authorized third parties to track the user's progress towards complete medication compliance.

In a separate embodiment, the current invention is a medication box by itself, where the medication box is characterized as discussed previously.

In yet another embodiment, the current invention can be a system or medication box that improves medication compliance, including any one or more—or even all—of the foregoing characteristics and functions.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 3B is a side view of the medication box with the paper of FIG. 3A positioned thereunder.

DETAILED DESCRIPTION OF THE PREFERRED EMBODIMENT

Figure 1A:
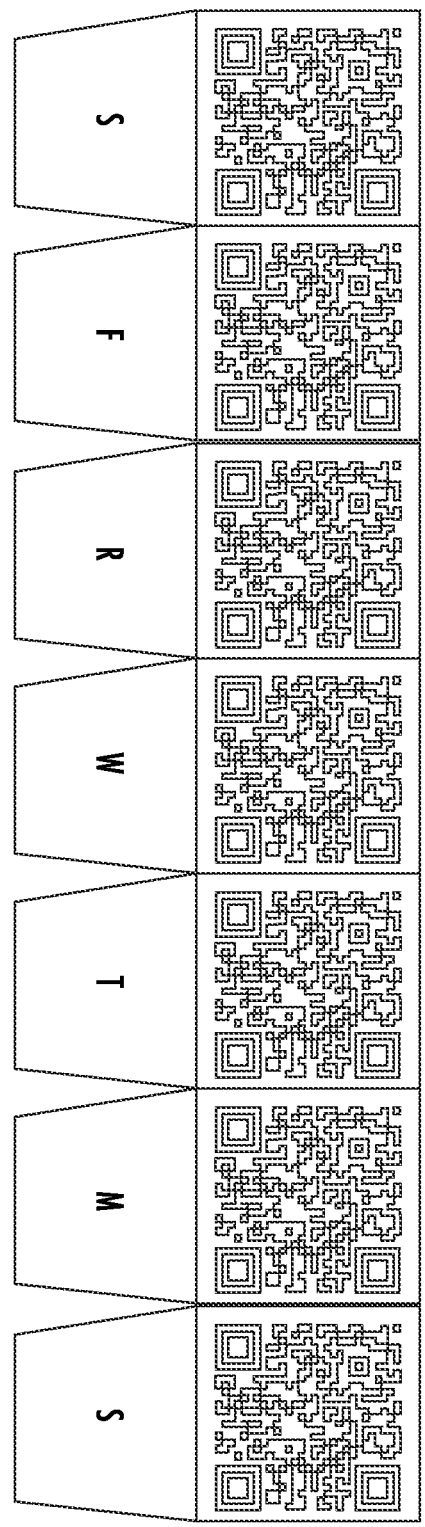
FIG. 1A is a top view schematic of an embodiment of the current invention.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

It is an object of the current invention to provide a device that fuses behavioral technology with automation to achieve the full promise of smart medication devices. In other words, what is provided is a medication management system that creates a synergy of automated prompts and behavior management technology to create a product yielding high medication compliance rates. It is a further object of the current invention to address the problem of low medication compliance in individuals who may be unmotivated to consume medication, which may be a function of their medical condition or injuries.

In certain embodiments, the current invention is a medication adherence system including a transparent medication box, which permits a machine-readable marker, such as a Quick Response (QR) code or other machine-readable code, to be read through the floors of individual medication containers in the medication box. This can be seen in FIGS. 1A-1B and 2. In use, once a patient empties an individual medication chamber by removing the medications contained therein, the machine-readable marker contained on the floor of each individual chamber is exposed and can be read using a combination reader/display device equipped with a digital camera, such as a smartphone. If medications are still contained in the individual medicine chambers, the machine-readable marker cannot be read and thus, in this sense, the machine-readable marker functions as a type of "sensor" to determine the presence of medications remaining in the chamber (a yes/no function). This yes/no function is important to the success of the behavior management system utilized, such as a token economy, as will be described below.

Once the individual medication chamber is empty, the combination reader/display device is placed over the empty chamber and scans the marker. This marker/barcode includes data pertaining to the medication, the user's medication plan (e.g., what medication the user should be taking and when) and timestamps. Scanning the marker automatically acquires information embedded in the marker. The data in the machine-readable marker contains, but is not limited to, the date and time on which the medication should be taken.

Figure 1B:
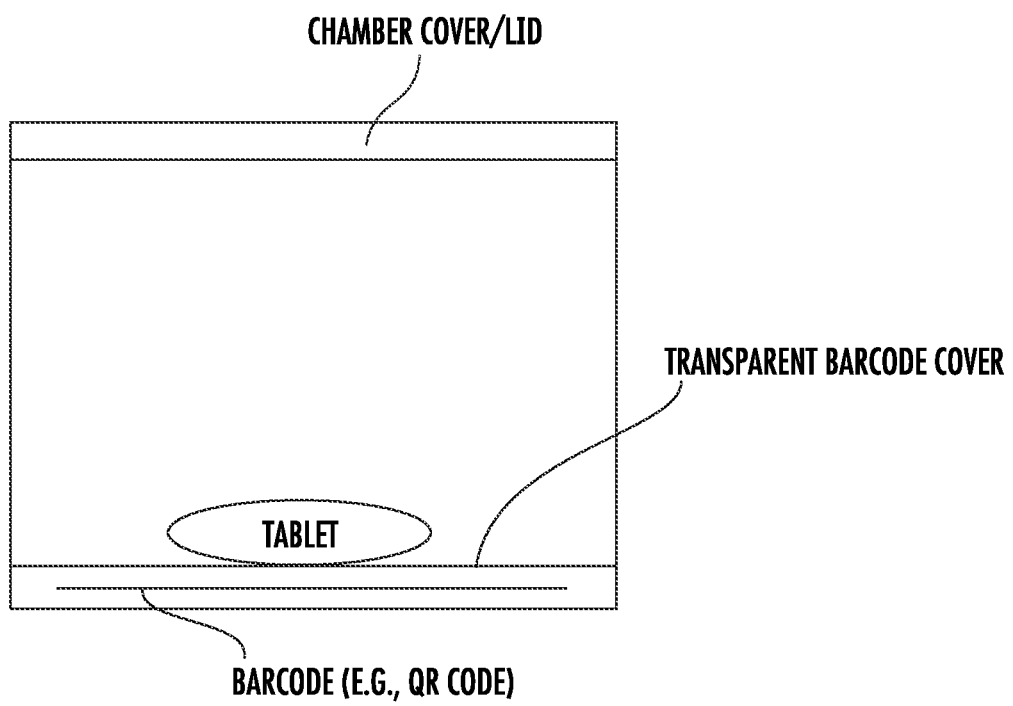
FIG. 1B is a cross-sectional schematic of one chamber of the embodiment of FIG. 1A.
Figure 2:
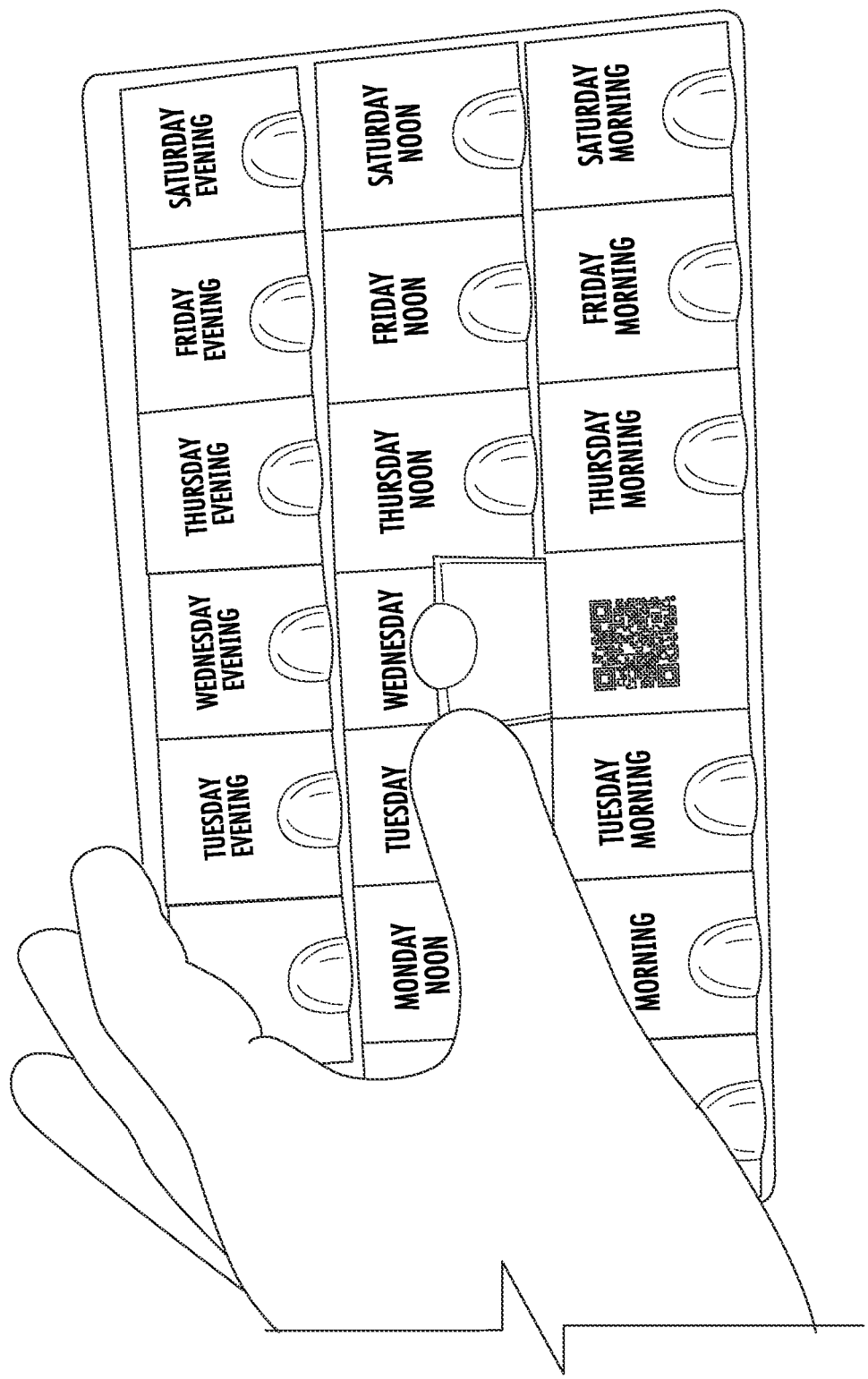
FIG. 2 is an image depicting a prototype of an QR codes in a medication box, according to an embodiment of the current invention.

Structurally, as illustrated in FIGS. 1A-1B, the marker can be disposed in overlying relation to the bottom surface of each chamber of the medication container, where a transparent marker cover is disposed in overlying relation to the marker. The medication is then positioned atop the marker cover. Thus, when the medication is removed, the marker is exposed and can be accessed. In an alternative embodiment, as may be indicated in FIG. 1A, the marker is laser engraved, laser etched, or otherwise permanently imposed on the bottom surface of each chamber.

Figure 3A:
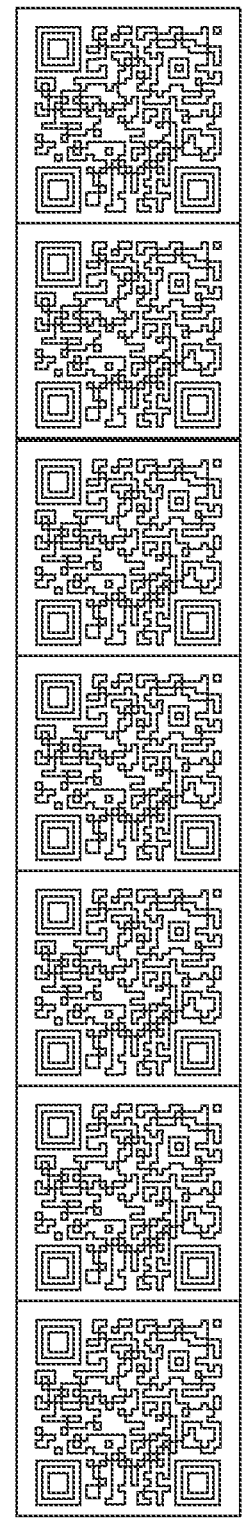
FIG. 3A is an elevated view of a paper with QR codes printed thereon.

In other embodiments, a single sheet of paper containing all markers would be adhered to the underside of the clear container so that the markers line up with the chambers. At the end of the medication sequence (e.g., week), the paper would be removed and replaced with the following week's medication schedule on a new piece of paper with markers. This can be seen in FIGS. 3A-3B.

Figure 4:
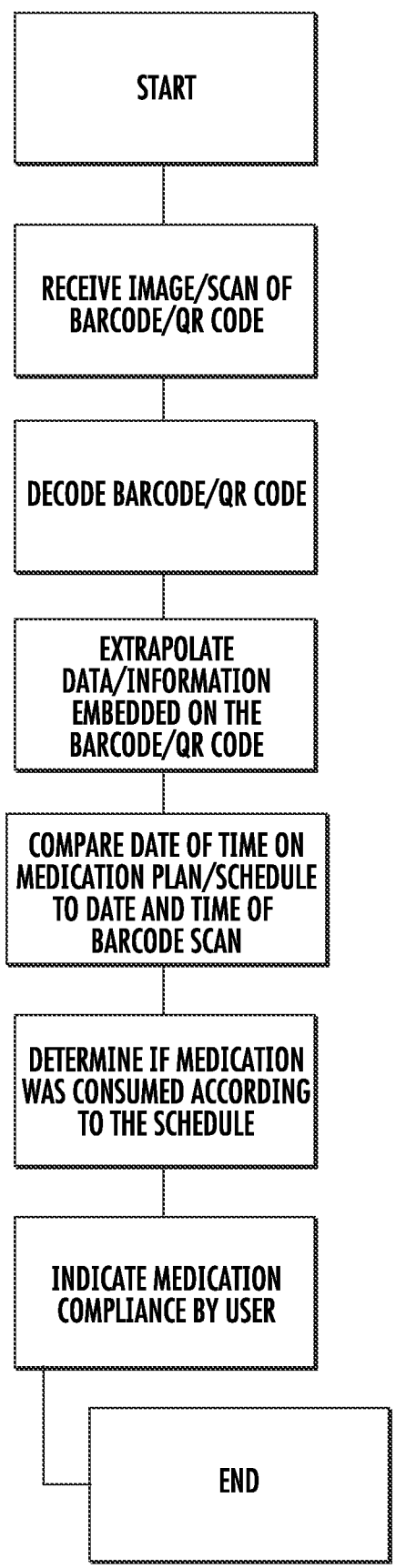
FIG. 4 is a flowchart depicting an algorithm of a software application, according to an embodiment of the current invention.

In certain embodiments, the current invention further includes a software program with the associated algorithm and hardware (see FIG. 4). The software program can be implemented as a mobile application that is installed on a mobile device, such as a smartphone. The software application deciphers the time and date information encoded in the machine-readable marker for that specific medication chamber (i.e., the date and time at which the medication is intended to be ingested by the user), and compares this information against the current date and time (i.e., the timestamp at which the marker is scanned and read). This comparison determines if medications were consumed according to the schedule embedded on the machine-readable marker and preset for the user.

The compliance information is integrated into a "reinforcement" module built into the software application, which is designed according to "Applied Behavior Analysis" behavioral technology positive reinforcement protocols that have been demonstrated in research studies to increase medication compliance by 20%. The reinforcement program in the current application provides behavioral prompts and motivational information to the user via the display on the mobile device, which are linked to the behavioral reinforcement contingencies established with caregivers and the patient themselves. Users could earn monetary rewards, token rewards for trading in for monetary or other higher preferred items, or other items that are found to be preferred by users. The reinforcement schedule could also be adjusted in the program to provide either fixed or variable schedules of reinforcement. Variable schedules of reinforcement have been found to be most successful in maintaining behavior over longer periods of time. The recorded compliance information can also build a historical log and a set of data analytics on associated websites and cloud-based data storage and analysis architectures, thus permitting the user or other authorized persons to track the user's progress towards complete medication adherence. This data could also be used to provide additional reinforcement for extended medication compliance.

Hardware and Software Infrastructure Examples

The present invention may be embodied on various computing platforms that perform actions responsive to software-based instructions and most particularly on touchscreen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object-oriented programming language such as Java, C #, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

Glossary of Claim Terms

Authorized third party: This term is used herein to refer to an individual or entity that has explicit permission to access the historical log and/or medical records of a user or patient.

Complete medication compliance: This term is used herein to refer to 100% or near 100% (e.g., >75%) adherence by a user/patient to a preset medication plan.

Machine-readable marker: This term is used herein to refer to a visual representation of data that is capable of being scanned or read by a camera or other image-capturing device, where scanning/reading of the marker results in the data itself being accessible to the user.

Medication plan: This term is used herein to refer to a set of instructions or actions that dictate what, when, and how certain medicine should be taken by a user.

Platform: This term is used herein to refer to a computing environment where data can be stored and optionally visualized. Examples include applications, websites, or software intended for such use.

Reinforcement module: This term is used herein to refer to a component of a computing system that functions to reinforce a targeted behavior (e.g., medication compliance) by a user.

Sequentially-ordered: This term is used herein to refer to a configuration of multiple chambers of a medication box according to a predetermined pattern, such as days of the week or timing of the medication to be consumed.

The disclosures of all publications cited above are expressly incorporated herein by reference, each in its entirety, to the same extent as if each were incorporated by reference individually. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

While there has been described and illustrated specific embodiments of the invention, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

It is also to be understood that the following claims are intended to cover all of the generic and specific features of the invention herein described, and all statements of the scope of the invention which, as a matter of language, might be said to fall there between. Now that the invention has been described,

What is claimed is:

1. A medication box, comprising:
   an array of sequentially-ordered, transparent chambers and one or more lids for covering top sides of the array of chambers;
   an array of machine-readable markers disposed along bottom sides of the array of chambers and configured to be scanned by an image-capturing device, wherein one machine-readable marker is provided for each chamber, wherein each machine-readable marker is embedded with data pertaining to a medication plan of a user of the medication box, and wherein the data includes identification of medication to be contained within a corresponding chamber, a date and time that the medication is scheduled to be ingested by the user, and instructions for the image-capturing device to record a date and time at which the machine-readable marker is scanned by the image-capturing device; and
   a paper with the machine-readable markers printed thereon, wherein the paper is disposed in underlying relation to the bottom sides of the array of chambers such that the machine-readable markers are aligned with the chambers, and wherein the user can access the each marker through each bottom side of the each chamber.

2. A medication box as in claim 1, wherein the array of machine-readable markers is an array of quick response codes.

3. A medication box as in claim 1, wherein the array of machine-readable markers is an array of barcodes.

4. A medication box as in claim 1, wherein the array of machine-readable markers is an array of machine-readable codes.

5. A medication box as in claim 1, wherein the array of machine-readable markers is an array of permanent markers.

6. A medication box as in claim 1, wherein the paper is adhered to the bottom sides of the array of chambers.

7. A medication box as in claim 6, wherein the paper is removably adhered to the bottom sides of the array of chambers.

8. A medication box as in claim 1, wherein the one or more lids comprises a plurality of lids for covering the top sides of the array of chambers.

9. A medication box as in claim 8, wherein one lid is provided for each chamber.

10. A system, comprising:
    an image-capturing device; and
    a medication box comprising:
      an array of sequentially-ordered, transparent chambers and one or more lids for covering top sides of the array of chambers;
      an array of machine-readable markers disposed along bottom sides of the array of chambers and configured to be scanned by the image-capturing device, wherein one machine-readable marker is provided for each chamber,
      wherein each machine-readable marker is embedded with data pertaining to a medication plan of a user of the medication box, and wherein the data includes identification of medication to be contained within a corresponding chamber, a date and time that the medication is scheduled to be ingested by the user, and instructions for the image-capturing device to record a date and time at which the machine-readable marker is scanned by the image-capturing device.

* * * * *